(12) United States Patent
Lin et al.

(10) Patent No.: US 11,752,183 B2
(45) Date of Patent: Sep. 12, 2023

(54) COMPOSITIONS OF PLANT EXTRACTS FOR REDUCING UV DAMAGE

(71) Applicant: TCI CO., LTD, Taipei (TW)

(72) Inventors: Yung-Hsiang Lin, Taipei (TW); I-Hui Chen, Taipei (TW); Kai-Wen Kan, Taipei (TW); Fu Chen Liu, Taipei (TW); Ciao-Ting Chen, Taipei (TW)

(73) Assignee: TCI CO., LTD, Taipei (TW)

( * ) Notice: Subject to any disclaimer, the term of this patent is extended or adjusted under 35 U.S.C. 154(b) by 0 days.

(21) Appl. No.: 16/499,990

(22) PCT Filed: Apr. 3, 2018

(86) PCT No.: PCT/CN2018/081708
§ 371 (c)(1),
(2) Date: Oct. 1, 2019

(87) PCT Pub. No.: WO2018/184522
PCT Pub. Date: Oct. 11, 2018

(65) Prior Publication Data
US 2020/0108280 A1    Apr. 9, 2020

Related U.S. Application Data

(60) Provisional application No. 62/503,185, filed on May 8, 2017, provisional application No. 62/480,860, filed on Apr. 3, 2017.

(51) Int. Cl.
| | | |
|---|---|---|
| A61K 36/185 | (2006.01) |
| A23L 33/105 | (2016.01) |
| A61K 9/00 | (2006.01) |
| A61K 9/08 | (2006.01) |
| A61K 9/48 | (2006.01) |
| A61P 3/04 | (2006.01) |
| A61K 31/01 | (2006.01) |
| A61K 31/015 | (2006.01) |
| A61K 36/21 | (2006.01) |
| A61K 36/258 | (2006.01) |
| A61K 36/31 | (2006.01) |
| A61K 36/45 | (2006.01) |
| A61K 36/48 | (2006.01) |
| A61K 36/53 | (2006.01) |
| A61K 36/67 | (2006.01) |
| A61K 36/73 | (2006.01) |
| A61K 36/74 | (2006.01) |
| A61K 36/752 | (2006.01) |
| A61K 36/815 | (2006.01) |
| A61K 36/82 | (2006.01) |
| A61K 36/87 | (2006.01) |
| A61K 36/886 | (2006.01) |
| A61K 36/8962 | (2006.01) |
| A61K 36/9066 | (2006.01) |
| A61K 8/9789 | (2017.01) |
| A61P 17/16 | (2006.01) |
| A61Q 19/00 | (2006.01) |
| A23F 3/16 | (2006.01) |
| A61K 8/97 | (2017.01) |

(Continued)

(52) U.S. Cl.
CPC ............ A61K 36/185 (2013.01); A23F 3/163 (2013.01); A23L 33/105 (2016.08); A61K 8/97 (2013.01); A61K 8/9789 (2017.08); A61K 9/0056 (2013.01); A61K 9/0095 (2013.01); A61K 9/08 (2013.01); A61K 9/48 (2013.01); A61K 31/01 (2013.01); A61K 31/015 (2013.01); A61K 36/21 (2013.01); A61K 36/258 (2013.01); A61K 36/31 (2013.01); A61K 36/45 (2013.01); A61K 36/48 (2013.01); A61K 36/53 (2013.01); A61K 36/67 (2013.01); A61K 36/73 (2013.01); A61K 36/74 (2013.01); A61K 36/752 (2013.01); A61K 36/815 (2013.01); A61K 36/82 (2013.01); A61K 36/87 (2013.01); A61K 36/886 (2013.01); A61K 36/8962 (2013.01); A61K 36/9066 (2013.01); A61P 3/04 (2018.01); A61P 17/16 (2018.01); A61P 19/04 (2018.01); A61Q 17/04 (2013.01); A61Q 19/007 (2013.01); A61Q 19/08 (2013.01); A23V 2002/00 (2013.01)

(58) Field of Classification Search
CPC ...................................................... A61K 36/00
USPC ......................................................... 424/725
See application file for complete search history.

(56) References Cited

U.S. PATENT DOCUMENTS

| | | | |
|---|---|---|---|
| 9,381,144 B1 * | 7/2016 | Hilt ...................... A61K 8/671 |
| 2005/0048008 A1 | 3/2005 | Gupta | |
| 2008/0138393 A1 | 6/2008 | Fast et al. | |

FOREIGN PATENT DOCUMENTS

| | | |
|---|---|---|
| CN | 1173991 | 2/1998 |
| CN | 1173991 A | 2/1998 |

(Continued)

OTHER PUBLICATIONS

Wang, Liuxiang, "Protective Effect of EGCG against Oxidative Damages Induced by UVA in Human Skin Fibroblast", Feb. 15, 2014, No. 02, Medicine & Public Health, China Master's Theses Full-Text Database.

(Continued)

*Primary Examiner* — Michael V Meller
(74) *Attorney, Agent, or Firm* — Chieh-Mei Wang

(57) ABSTRACT

Provided is a plant extract-containing composition for reducing skin damage caused by ultraviolet radiation. The composition includes a combination of extracts of spinach, black tea, green tea, Pu-erh tea, Four Seasons Spring tea, red wine, blueberry, grape seeds, citrus, or green coffee beans.

2 Claims, 1 Drawing Sheet

(51) Int. Cl.
  *A61Q 17/04* (2006.01)
  *A61P 19/04* (2006.01)
  *A61Q 19/08* (2006.01)

(56) References Cited

FOREIGN PATENT DOCUMENTS

| | | | |
|---|---|---|---|
| CN | 101843298 A | | 9/2010 |
| CN | 102091006 A | | 6/2011 |
| CN | 102125586 A | | 7/2011 |
| CN | 102258196 A | | 11/2011 |
| CN | 102258638 A | | 11/2011 |
| CN | 102578645 A | | 7/2012 |
| CN | 102578645 A | | 7/2012 |
| CN | 102763885 A | | 11/2012 |
| CN | 102763885 A | | 11/2012 |
| CN | 103222930 A | | 7/2013 |
| CN | 103405363 A | | 11/2013 |
| CN | 103735687 A | | 4/2014 |
| CN | 103735687 A | | 4/2014 |
| CN | 103876020 A | | 6/2014 |
| CN | 103987385 A | | 8/2014 |
| CN | 104106691 | * | 10/2014 |
| CN | 104109609 | * | 10/2014 |
| CN | 104365753 A | * | 2/2015 |
| CN | 104397565 A | | 3/2015 |
| CN | 104800146 A | | 7/2015 |
| CN | 104800146 A | | 7/2015 |
| CN | 105285211 A | | 2/2016 |
| CN | 105454784 A | | 4/2016 |
| CN | 105494827 A | | 4/2016 |
| CN | 105878087 A | | 8/2016 |
| CN | 106075179 A | | 11/2016 |
| CN | 106165869 A | | 11/2016 |
| CN | 106265415 A | | 1/2017 |
| FR | 2906143 | * | 3/2008 |
| JP | 2001200238 A | | 7/2001 |
| KR | 20160021734 A | | 2/2016 |
| TW | 200816926 A | | 4/2008 |

OTHER PUBLICATIONS

Xu, Qingping et al., "Antioxidant Activity of Spinach Extracts", Modern Food Science and Technology, 23 (2), Feb. 15, 2007, p. 31-32 and 36.
Pu, Bingqing et al., "Analyse and Compared the Tea Polyphenol Contents and Caffeine in Different Varieties of Tea", The Food Industry, 38 (2), Feb. 20, 2017, p. 301-303.
Chen, Mingliang et al., "Effect of Resveratrol on Fibroblasts Proliferation and iNOS Gene Expression in Skin Fibroblasts after UVA Irradition", Chinese Pharmaceutical Journal, 44(16), Aug. 31, 2009, p. 1226-1229.
Kubo, M., "Whitening Effect of Citrus Fruit", International Journal of Traditional Chinese Medicine, 28(6), Nov. 30, 2006, p. 367.
Examination report dated Apr. 28, 2022, listed in correspondent Taiwan patent application No. 110118933 (publication No. TW 202137976 A).
Naringenin Protects HaCaT Human Keratinocytes Against UVB-induced Apoptosis and Enhances the Removal of Cyclobutane Pyrimidine Dimers from the Genome, Mohamed A. El-Mahdy,et al., Photochem Photobiol, 2008, 84(2): 307-316. Abstract; the last 2nd paragraph of Introduction; paragraph 1-4 of Discussion; the last 2nd paragraph of Discussion.
Myricetin suppresses UVB-induced wrinkle formation and MMP-9 expression by inhibiting Raf, Sung Keun Jung,et al., Biochem Pharmacol, May 15, 2010, 79(10): 1455-1461. Abstract; the fourth paragraph of Introduction.
EESR dated Jul. 8, 2022, listed in related European patent application No. 22 165 424.7(publication No. EP4039261).
Evaluation of black tea gel and its protection potential against UV, M. Turkoglu et al., International Journal of Cosmetic Science, 2007, vol. 29, pp. 437-442 Abstract.

Database GNPD [Online], Mintel; Dec. 1, 2016, Anonymous: VT Galaxy Skin, XP055732253, Database accession No. 4459435 Abstract.
Protective effects of citrus and rosemary extracts on UV-induced damage in skin cell model and human volunteers, A. Pérez Sánchez et al., Journal of Photochemistry and Photobiology B:Biology, 2014, vol. 136, pp. 12-18 the whole document.
Dietary polyphenols as photoprotective agents against UV radiation, Shuting Hu et al., Journal of Functional Foods, 2017, vol. 30, pp. 108-118 Table 1.
Partial supplementary search report dated Oct. 5, 2020, listed in correspondent European patent application No. 18781720.0 (publication No. EP3607958).
Database GNPD [Online], Mintel; Jun. 20, 2016 Anonymous: Perfect Proof Sun Block SPF50+/PA+++, XP055732257, retrieved from www.gnpd.com Database accession No. 3986205.
Examination report dated Dec. 17, 2020, listed in correspondent Taiwan patent application No. 107111687 (publication No. TW201836590).
Examination report dated Jun. 1, 2021, listed in correspondent China patent application No. 201880021268.X (publication No. CN 110461347 A).
Dark Green Vegetables Help You Resist Cataracts, New World, Zhu Feng, Sep. 30, 2006 First paragraph.
Be your own Nutritionist, Ming Chang, Jan. 31, 2014, Tianjin Science and Technology Press Last 2 paragraphs from the left column to the first paragraph from the right column on p. 710.
Light and Heat Countermeasures for Beverage, Food Global Industry, Jian-Hui Dong, Jan. 31, 2002 Last 3 paragraphs from the right column on p. 64.
Effect of Grape Seed Proanthocyanidins Extracts on TGF-β R II and Smad7 Expression in Human Skin Fibroblasts Induced by Ultraviolet A, Chinese Journal of Dermatovenereology of Integrated Traditional and Western Medicine, Dec. 31, 2015, Kang et al. Abstract.
Blueberries and Sweet Oranges Can Prevent Sunburn, China Fruit News, RUI SI, Sep. 30, 2014 First and second paragraphs.
The extended European search report dated Mar. 12, 2021, listed in correspondent European patent application No. 18781720.0 (publication No. EP3607958).
Database GNPD [Online] Mintel; Feb. 8, 2017, anonymous: Light Mousse Cream SPF 15, XP055775625, Database accession No. 4543791, abstract.
Database GNPD [Online] Mintel; Apr. 16, 2012, anonymous: Perfect C Serum, XP055775634, Database accession No. 1777550, abstract.
Tomaino A et al.: In vitro protective effect of a Jacquez grapes wine extract on UVB-induced skin damage. Toxiocology in Vitro, Elsevier Science, GB, vol. 20, No. 8, Dec. 1, 2006, pp. 1395-1402. XP024966278. ISSN: 0887-2333, DOI: 10. 1016/J. TIV. 2006.06.005 [retrieved on Dec. 1, 2006], abstract.
Apraj Vinita D et al.: Evaluation of Skin Anti-aging Potential of Citrus reticulata Blanco Peel Correspondence. Jul.-Sep., Jan. 1, 2016, pp. 160-168, XP055775655, Retrieved from the Internet: URL: https: //www.ncbi.nlm.nih.gov/pmc/articles/PMC4908842/?report=printable [retrieved on Feb. 12, 2021], abstract.
Hu Shuting et al.: Dietary polyphenols as phtoprotective agents against UV radiation. Journal of Functional Foods, Elsevier BV, NL, vol. 30, Jan. 12, 2017, pp. 108-118, XP029908072, ISSN: 1756-4646, DOI: 10.1016/J.JFF.2017.01.009, see Table 1.
Examination report dated Dec. 7, 2021, listed in correspondent European patent application No. 18781720.0 (publication No. EP3607958).
Julie Foucquier et al: "Analysis of drug combinations: current methodological landscape", Pharmacology Research & Perspectives, vol. 3, No. 3, May 20, 2015 (May 20, 2015), pp. 1-11, XP055462926, GB ISSN: 2052-1707, DOI: 10.1002/prp2.149.
Madhulika Singh et al.: "New Enlightenment of Skin Cancer Chemoprevention through Phytochemicals: In Vitro and In Vivo Studies and the Underlying Mechanisms", BioMed Research Inter-

(56) References Cited

OTHER PUBLICATIONS national, vol. 2014, Jan. 1, 2014 (Jan. 1, 2014), pp. 1-18, XP055732673, ISSN: 2314-6133, DOI: 10.1155/2014/243452.

* cited by examiner

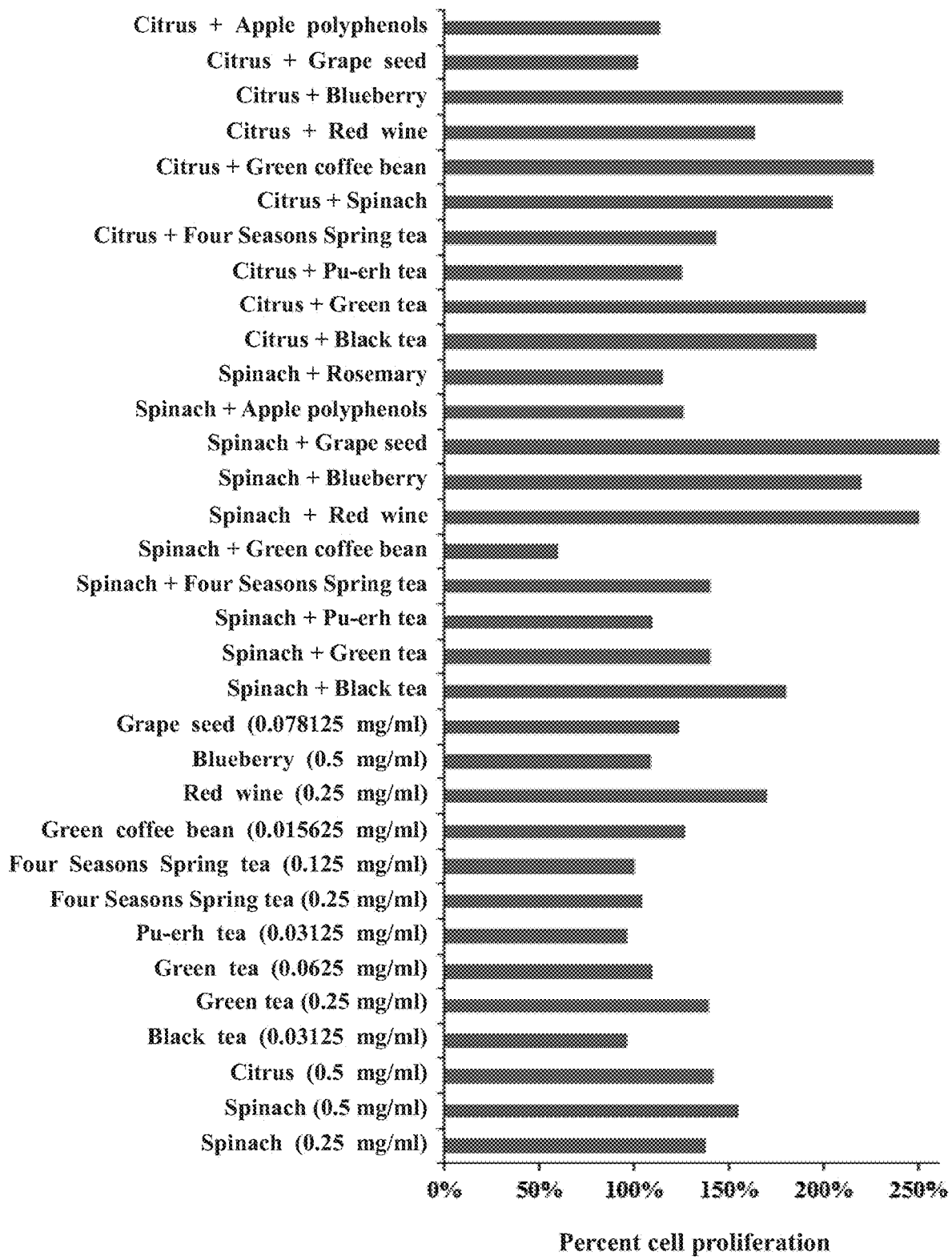

COMPOSITIONS OF PLANT EXTRACTS FOR REDUCING UV DAMAGE

CROSS-REFERENCE TO RELATED APPLICATION

This application claims priority of U.S. Provisional Application No. 62/480,860, filed on Apr. 3, 2017, and U.S. Provisional Application No. 62/503,185, filed on May 8, 2017, the content of which is incorporated herein in its entirety by reference.

BACKGROUND OF THE INVENTION

1. Field of the Invention

The present invention relates to a composition containing plant extracts and applications thereof, and in particular, relates to a composition for reducing skin damage caused by ultraviolet radiation and applications thereof.

2. The Prior Art

The sun is the principle source of ultraviolet (UV) exposure for most people. Ultraviolet light is subdivided into ultraviolet A (UVA; wavelength, 315-400 nm), ultraviolet B (UVB; 280-315 nm), and ultraviolet C (UVC; 100-280 nm). Ultraviolet C is absorbed by the atmosphere and does not reach the surface of the earth. Ultraviolet B is the most damaging UV to living organisms, but is mostly absorbed by the atmosphere. The long-wavelength ultraviolet A is the most intense UV reaching the earth and can penetrate deep into tissues of the body. Studies have found that UV exposure accelerates skin aging and increases the risk of skin cancer, and may reduce individuals' resistance to infectious diseases.

The skin is a large organ with an area of more than 1.5 $m^2$ in adults that provides the first-line protection against UV radiation from the sun. The skin includes the epidermis (including the outermost horny layer), the dermis, and the subcutaneous tissue. The epidermis is the outermost layer of the skin and is constantly renewed. Between the epidermis and the dermis reside persistently dividing cells (such as fibroblasts, keratinocytes, and melanocytes), whose activities are very sensitive to ultraviolet light. The dermis contains collagen and elastin, both of which impart elasticity and support to the skin. By enhancing melanin production and promoting cell proliferation to thicken the outer skin layer (the horny layer), the skin protects tissue below the epidermis from UV-induced damage. For example, when exposed to high amounts of UV (mainly UVA), collagen fibers and elastin are damaged, resulting in reduced skin elasticity, wrinkle formation, and appearance of skin aging.

Sun exposure avoidance and use of sunscreens are the most common strategies to reduce damage by UV radiation. For adequate protection, sunscreens with even thickness need to be applied to large areas of skin and allowed to dry for about 15 minutes before recipients go outside. In addition, a second application at intervals is needed to maintain the thickness of sunscreens. Most people get improper protection as failing to use sunscreens in the manner described above. In some cases, sunscreens contain chemicals that may cause photosensitivity, so that the combination of these chemicals with UV poses an adverse effect to the skin, such as a rash or more severe sunburn.

In view of this, it is of necessity to develop a composition that includes natural ingredients and is effective in protecting the skin from UV damage, so as to retard skin aging or reduce the incidence of skin cancer.

SUMMARY OF THE INVENTION

Accordingly, in one aspect, the present invention provides a composition including a plant extract, wherein the composition includes a combination selected from the group consisting of a spinach extract and a black tea extract, a spinach extract and a red wine extract, a spinach extract and a blueberry extract, a spinach extract and a grape seed extract, a citrus extract and a black tea extract, a citrus extract and a green tea extract, a citrus extract and a Pu-erh tea extract, a citrus extract and a Four Seasons Spring tea extract, a citrus extract and a red wine extract, a citrus extract and a green coffee bean extract, a citrus extract and a spinach extract, and a citrus extract and a grape seed extract.

In one embodiment of the present invention, the composition including the spinach extract includes one of the following combinations: at least 0.078125 mg/ml of the spinach extract and at least 0.078125 mg/ml of the grape seed extract; at least 0.25 mg/ml of the spinach extract and at least 0.25 mg/ml of any one of the black tea extract and the red wine extract; or at least 0.5 mg/ml of the spinach extract and at least 0.5 mg/ml of the blueberry extract.

In one embodiment of the present invention, the composition including the citrus extract includes one of the following combinations: at least 0.015625 mg/ml of the citrus extract and at least 0.015625 mg/ml of the green coffee bean extract; at least 0.03125 mg/ml of the citrus extract and at least 0.03125 mg/ml of the Pu-erh tea extract; at least 0.0625 mg/ml of the citrus extract and at least 0.0625 mg/ml of any one of the black tea extract and the green tea extract; at least 0.078125 mg/ml of the citrus extract and at least 0.078125 mg/ml of the grape seed extract; at least 0.125 mg/ml of the citrus extract and at least 0.125 mg/ml of the Four Seasons Spring tea extract; or at least 0.25 mg/ml of the citrus extract and at least 0.25 mg/ml of any one of the red wine extract and the spinach extract.

In another aspect, the present invention provides a pharmaceutical composition, including any one of the abovementioned composition and a pharmaceutically acceptable carrier.

In one embodiment of the present invention, the pharmaceutical composition may be in the form of a solution, a powder, a capsule, or a tablet.

In yet another aspect, the present invention provides use of any one of the abovementioned composition for reducing damage to skin fibroblasts caused by ultraviolet radiation, or use of any one of the abovementioned composition in the manufacture of a pharmaceutical composition for protecting skin from damage by ultraviolet radiation.

In one embodiment of the present invention, the ultraviolet radiation is ultraviolet A radiation.

Due to the mix of particular plant extracts, the composition of the invention greatly inhibits the death of skin fibroblasts caused by ultraviolet irradiation. The normal proliferation of skin fibroblasts then contributes to maintaining the thickness and the UV barrier function of the epidermis, as well as supplementing the composition of the extracellular matrix of the skin and maintaining the renewal of the dermis. In other words, administration of an effective amount of the composition of the invention to a subject significantly reduces skin damage caused by ultraviolet radiation. Therefore, the composition of the invention may be used in the manufacture of a pharmaceutical composition for protecting skin from damage by ultraviolet radiation.

BRIEF DESCRIPTION OF THE DRAWINGS

The accompanying drawings form part of the present specification and are included here to further demonstrate some aspects of the present invention, which can be better understood by reference to one or more of these drawings, in combination with the detailed description of the embodiments presented herein.

FIG. 1 shows the effect of the various compositions according to one embodiment of the invention on the percent proliferation of UV-irradiated skin fibroblasts.

DETAILED DESCRIPTION OF THE PREFERRED EMBODIMENT

The embodiments of the present invention are further described below, in reference to the accompanying drawings. Examples are set forth below to illustrate the features and applications of the present invention, and are not intended to limit the scope of the present invention. Those of ordinary skill in the art will appreciate that various changes and modifications may be made without departing from the spirit or scope of the present disclosure, which is defined in the appended claims.

Definition

Numerical quantities provided herein are approximated values. All experimental values may vary within 20 percent, preferably within 10 percent, and most preferably within 5 percent of the given values.

As used herein, "pharmaceutically acceptable carrier" refers to one or more solid or liquid vehicles which are not toxic to mammals and which do not affect the biological activity of an active ingredient in a composition.

The present invention provides a composition for reducing skin damage caused by ultraviolet radiation. The composition contains a plurality of plant extracts. The composition is prepared by mixing the extract of spinach, black tea, green tea, Four Seasons Spring tea, red wine, blueberry, grape seeds, citrus, or green coffee beans. The following examples disclose that said composition can greatly inhibit the death of skin fibroblasts caused by ultraviolet A irradiation.

Materials and Methods

Materials

Eagle's minimum essential medium containing Earle's balanced salt solution (referred to as MEM), fetal bovine serum (FBS), penicillin/streptomycin, and phosphate buffered saline (PBS) were purchased from Gibco. 3-(4,5-dimethylthiazol-2-yl)-2,5-diphenyltetrazolium bromide (MTT) used in cell viability assay was purchased from AMERSCO. Dimethyl sulfoxide (DMSO) was purchased from Echo Chemical. Apple polyphenols were purchased from Giwan Ltd.

Cell Culture

In the following examples, the experiment was performed using human skin fibroblasts CCD-966SK (ATCC CRL-1881). The human skin fibroblasts were cultured at 37° C. under 5% carbon dioxide in MEM supplemented with 10% FBS and 1% penicillin/streptomycin, hereinafter referred to as cell culture medium.

MTT Assay

The cell viability or percent cell proliferation was measured by MTT assay. Briefly, an MTT solution (4 mg/ml MTT in PBS) was added to cells in a 96-well plate at 15 μl/well for a reaction at room temperature for 4 hours. After the reaction solution was discarded, DMSO was added to the cells at 50 μl/well and incubated with shaking for 10 minutes to dissolve the resulted formazan crystals. Lastly, the absorbance of the cell suspension at 570 nm (O.D. 570) was measured using an ELISA (enzyme-linked immunosorbent assay) reader (BioTek). The statistical significance of differences between data was determined by Student's t-test using the Excel software.

Example 1 Preparations of Plant Extracts 1-1 Spinach Extract

The spinach extract is obtained by extracting spinach (*Spinacia oleracea*). The extract may be purchased from Hong Siang Farm Products Factory.

1-2 Black Tea Extract

This example exemplifies the method of preparing a black tea extract. Black tea leaves (the fermented leaves of *Camellia sinensis*) are first washed, dried, and crushed coarsely with a pulverizer. Next, the coarsely crushed black tea leaves are extracted with water as the solvent, wherein the solvent and the coarsely crushed black tea leaves are mixed uniformly at a liquid-solid ratio of 5-20:1-5, and the extraction temperature is between 50° C. and 100° C., preferably between 75° C. and 95° C. The extraction time is about 0.5 to 3 hours. After cooled to room temperatures, the black tea extract obtained from the extraction step is filtered through a 400 mesh filter to remove solid residues. The filtered black tea extract may further be concentrated under reduced pressure at 45° C. to 70° C. to obtain a concentrated product.

1-3 Green Tea Extract

This example exemplifies the method of preparing a green tea extract. Green tea leaves (the unfermented leaves of *Camellia sinensis*) are first washed, dried, and crushed coarsely with a pulverizer. Next, the coarsely crushed green tea leaves are extracted with water as the solvent, wherein the solvent and the coarsely crushed green tea leaves are mixed uniformly at a liquid-solid ratio of 5-20:1-5, and the extraction temperature is between 50° C. and 100° C., preferably between 75° C. and 95° C. The extraction time is about 0.5 to 3 hours. After cooled to room temperatures, the green tea extract obtained from the extraction step is filtered through a 400 mesh filter to remove solid residues. The filtered green tea extract may further be concentrated under reduced pressure at 45° C. to 70° C. to obtain a concentrated product.

1-4 Pu-Erh Tea Extract

The Pu-erh tea extract is obtained by extracting Pu-erh tea leaves (post-fermented leaves of *Camellia sinensis*). The extract may be purchased from Nanjing Zelang Biotechnology Co., Ltd.

1-5 Four Seasons Spring Tea Extract

This example exemplifies the method of preparing a Four Seasons Spring tea extract. Four Seasons Spring tea leaves (the leaves of the Four Seasons Spring tea plant) are first washed, dried, and crushed coarsely with a pulverizer. Next, the coarsely crushed Four Seasons Spring tea leaves are extracted with water as the solvent, wherein the solvent and the coarsely crushed Four Seasons Spring tea leaves are mixed uniformly at a liquid-solid ratio of 5-20:1-5, and the extraction temperature is between 50° C. and 100° C., preferably between 75° C. and 95° C. The extraction time is about 0.5 to 3 hours. After cooled to room temperatures, the Four Seasons Spring tea extract obtained from the extraction step is filtered through a 400 mesh filter to remove solid residues. The filtered Four Seasons Spring tea extract may further be concentrated under reduced pressure at 45° C. to 70° C. to obtain a concentrated product.

1-6 Red Wine Extract

The red wine extract is obtained by extracting red wines. The extract may be purchased from Shanghai Boyoutang Biotechnology Co., Ltd.

1-7 Green Coffee Bean Extract

The green coffee bean extract is obtained by extracting unroasted seeds of *Coffea* spp. plants. The extract may be purchased from ARJUNA NATURAL EXTRACTS Ltd (India).

1-8 Blueberry Extract

The blueberry extract is obtained by extracting the fruit of North American blueberry (*Vaccinium Cyanococcus*). The extract may be purchased from Biomed Herbal Research Co., Ltd.

1-9 Citrus Extract

The citrus extract is obtained by extracting the fruit of mandarin orange (*Citrus reticulata*). The extract may be purchased from Roterm Trading Co., Ltd.

1-10 Grape Seed Extract

The grape seed extract is obtained by extracting the seeds of *Vitis* spp. plants. The extract may be purchased from Guarante Biotech Co., Ltd.

1-11 Rosemary Extract

The rosemary extract is obtained by extracting rosemary (*Rosmarinus officinalis*). The extract may be purchased from Jiajing Baica Co., Ltd.

Example 2

Inhibition of the UVA-Induced Death of Skin Fibroblasts by Compositions Containing Plant Extracts To examine the protective effect of the composition of the invention on the skin against ultraviolet radiation, cell viability assay (MTT assay) was employed to assess the percent proliferation of human skin fibroblasts CCD-966SK first irradiated with UVA and then treated with the indicated plant extracts or combinations thereof. Briefly, CCD-966SK cells were seeded at $5 \times 10^3$ cells/well in 96-well culture plates, where each well contained 200 μl of cell culture medium. After incubation at 37° C. for 24 hours, the cell culture medium was removed and the cells were placed in a UV irradiation chamber (Vilber) and irradiated with 15 J/cm² UVA for 1 hour, which was a half lethal dose of radiation for the cells. Thereafter, each of the plant extracts or each of the compositions containing plant extracts, listed in TABLE 1, together with the cell culture medium were added to the cells, which were cultured at 37° C. for 24 hours. Another group of cells, set as a negative control, was irradiated with UVA but treated with a cell culture medium free of plant extracts; and still another group of cells, set as a mock control, was not irradiated with UVA and was treated with the cell culture medium free of plant extracts. Finally, MTT analysis was performed to determine the percent proliferation for each group of cells. The percent cell proliferation is calculated according to the following formula:

Percent cell proliferation=O.D. 570 for each group/ O.D. 570 for the negative control×100%

TABLE 1

| Treatments | | Percent cell proliferation |
|---|---|---|
| Mock control | | 237% |
| Negative control | | 100% |

TABLE 1-continued

| Treatments | | Percent cell proliferation |
|---|---|---|
| Spinach | 0.25 mg/ml | 138% |
|  | 0.5 mg/ml | 155% |
| Citrus | 0.5 mg/ml | 142% |
| Black tea | 0.03125 mg/ml | 96.39% |
| Green tea | 0.25 mg/ml | 139.36% |
|  | 0.0625 mg/ml | 110.04% |
| Pu-erh tea | 0.03125 mg/ml | 96.79% |
| Four Seasons Spring tea | 0.25 mg/ml | 104.02% |
|  | 0.125 mg/ml | 100.40% |
| Green coffee bean | 0.015625 mg/ml | 127.31% |
| Red wine | 0.25 mg/ml | 169.88% |
| Blueberry | 0.5 mg/ml | 109.24% |
| Grape seed | 0.078125 mg/ml | 123.69% |
| Spinach + Black tea 0.25 mg/ml + 0.25 mg/ml | | 180% |
| Spinach + Green tea 0.25 mg/ml + 0.25 mg/ml | | 140% |
| Spinach + Pu-erh tea 0.25 mg/ml + 0.25 mg/ml | | 110% |
| Spinach + Four Seasons Spring tea 0.25 mg/ml + 0.25 mg/ml | | 140% |
| Spinach + Green coffee bean 0.125 mg/ml + 0.125 mg/ml | | 60% |
| Spinach + Red wine 0.25 mg/ml + 0.25 mg/ml | | 250% |
| Spinach + Blueberry 0.5 mg/ml + 0.5 mg/ml | | 220% |
| Spinach + Grape seed 0.078125 mg/ml + 0.078125 mg/ml | | 168% |
| Spinach + Apple polyphenols 0.0625 mg/ml + 0.0625 mg/ml | | 126% |
| Spinach + Rosemary 0.125 mg/ml + 0.125 mg/ml | | 115% |
| Citrus + Black tea 0.0625 mg/ml + 0.0625 mg/ml | | 142% |
| Citrus + Green tea 0.0625 mg/ml + 0.0625 mg/ml | | 176% |
| Citrus + Pu-erh tea 0.03125 mg/ml + 0.03125 mg/ml | | 193% |
| Citrus + Four Seasons Spring tea 0.125 mg/ml + 0.125 mg/ml | | 143% |
| Citrus + Spinach 0.25 mg/ml + 0.25 mg/ml | | 204% |
| Citrus + Green coffee bean 0.015625 mg/ml + 0.015625 mg/ml | | 167% |
| Citrus + Red wine 0.25 mg/ml + 0.25 mg/ml | | 209% |
| Citrus + Blueberry 0.5 mg/ml + 0.5 mg/ml | | 93% |
| Citrus + Grape seed 0.078125 mg/ml + 0.078125 mg/ml | | 166% |
| Citrus + Apple polyphenols 0.0625 mg/ml + 0.0625 mg/ml | | 114% |

TABLE 1 shows the percent proliferation of skin fibroblasts after different treatments; FIG. 1 is a histogram corresponding to the values shown in TABLE 1. According to TABLE 1, the percent cell proliferation of the mock control relative to the negative control was 237%, indicating that UVA irradiation caused death of large numbers of skin fibroblasts. According to TABLE 1 and FIG. 1, compared to the negative control, the sole treatment with the spinach extract (0.25 mg/ml) or the citrus extract (0.5 mg/ml) increased the percent cell proliferation to 138% and 142%, respectively. In addition, the sole treatment with the black tea extract, the green tea extract, the Pu-erh tea extract, Four Seasons Spring tea extract, the green coffee bean extract, the blueberry extract, or the grape seed extract resulted in a percent cell proliferation ranging approximately between 95% and 140%. The sole treatment with the red wine extract resulted in a percent cell proliferation of about 170%.

It is worth noting that the combination of the spinach extract with the black tea extract, the blueberry extract, or the grape seed extract significantly increased the percent proliferation of skin fibroblasts to 180%, 220%, and 168%, respectively; and the combination of the spinach extract with the red wine extract increased the percent cell proliferation to about 250%. Similarly, the combination of the citrus extract, at a concentration equal to or far below 0.5 mg/ml, with the black tea extract, the green tea extract, the Pu-erh tea extract, the Four Seasons Spring tea extract, the green coffee bean extract, the spinach extract, or the grape seed extract significantly increased the percent cell proliferation to between 142% and 204%; and the combination of the citrus extract with the red wine extract increased the percent cell proliferation to about 209%. The compositions having the particular combinations set forth above unexpectedly exhibit higher UVA protective effect than the sum of the UVA protective effect for the respective single components.

In conclusion, due to the mix of particular plant extracts, the composition of the invention greatly inhibits the death of skin fibroblasts caused by ultraviolet irradiation. The normal proliferation of skin fibroblasts then contributes to maintaining the thickness and the UV barrier function of the epidermis, as well as supplementing the composition of the extracellular matrix of the skin and maintaining the renewal of the dermis. Therefore, the composition of the invention, along with a pharmaceutically acceptable carrier, may be used in the manufacture of a pharmaceutical composition for reducing skin damage caused by ultraviolet radiation. The pharmaceutical composition may be in the form of a solution, a powder, a capsule, or a tablet, but not limited thereto.

What is claimed is:

1. A method of treating skin damage caused by ultraviolet radiation in a human in need thereof, consisting essentially of administering to the human subject an therapeutically effective amounts of a pharmaceutical composition, wherein the pharmaceutical composition consists essentially of a pharmaceutically acceptable carrier and a combination selected from the group consisting of 0.25 mg/ml of a spinach extract and 0.25 mg/ml of a black tea extract, 0.5 mg/ml of a spinach extract and 0.5 mg/ml of a blueberry extract, 0.078125 mg/ml of a spinach extract and 0.078125 mg/ml of a grape seed extract, 0.0625 mg/ml of a citrus extract and 0.0625 mg/ml of a green tea extract, 0.125 mg/ml of a citrus extract and 0.125 mg/ml of a Four Seasons Spring tea extract, 0.25 mg/Ml of a citrus extract and 0.25 mg/ml of a red wine extract, and 0.25 mg/Ml of a citrus extract and 0.25 mg/ml of a spinach extract, wherein the blueberry extract is obtained by extracting fruit of North American blueberry (*Vaccinium Cyanococcus*).

2. The method of claim 1, wherein the ultraviolet radiation is ultraviolet A radiation.

* * * * *